US00PP30784P3

(12) United States Plant Patent
van Langen

(10) Patent No.: US PP30,784 P3
(45) Date of Patent: Aug. 6, 2019

(54) PACHYVERIA PLANT NAMED 'TSAECH1702'

(50) Latin Name: ***Pachyphytum glutinacaule* x *Echeveria hookeri***
Varietal Denomination: TSAECH1702

(71) Applicant: Tosjami B.V., Heerhugowaard (NL)

(72) Inventor: Gerard van Langen, Heerhugowaard (NL)

(73) Assignee: Tosjami B.V., Heerhugowaard (NL)

( * ) Notice: Subject to any disclaimer, the term of this patent is extended or adjusted under 35 U.S.C. 154(b) by 0 days.

(21) Appl. No.: 15/932,614

(22) Filed: Mar. 23, 2018

(65) Prior Publication Data

US 2018/0310454 P1 Oct. 25, 2018

(30) Foreign Application Priority Data

Apr. 25, 2017 (QZ) ..... PBR 2017/1147

(51) Int. Cl.
*A01H 5/12* (2018.01)
*A01H 6/00* (2018.01)
*A01H 6/32* (2018.01)

(52) U.S. Cl.
USPC ..... Plt./373
CPC ..... *A01H 6/00* (2018.05); *A01H 5/12* (2013.01); *A01H 6/32* (2018.05)

(58) Field of Classification Search
USPC ..... Plt./373
See application file for complete search history.

(56) References Cited

PUBLICATIONS

Plant Breeder's Art QZ PBR 20171147 on a *Pachyphytum* hybrid plant named 'TSAECH1702', published Jun. 16, 2017.*

* cited by examiner

*Primary Examiner* — Anne Marie Grunberg
(74) *Attorney, Agent, or Firm* — Samuel R. McCoy, Jr.

(57) ABSTRACT

A new and distinct *Pachyveria* plant *Pachyphytum glutinacaule* x *Echeveria hookeri,* named 'TSAECH1702' which is characterized by long and narrow succulent foliage with an upwardly curved aspect and an upright attitude, light greyed-green juvenile foliage with a white to light blue hue at and near the center of the rosette, foliage which becomes progressively suffused with yellow-green with age, mature foliage towards the outermost whorls of the rosette which is generally colored yellow-green with a blue hue, as well as the stability of these characteristics from generation to generation.

4 Drawing Sheets

Latin name of the genus and species: The Latin name of the genus and species of the novel variety disclosed herein is *Pachyphytum glutinacaule* x *Echeveria hookeri.*

Variety denomination

The inventive variety of *Pachyveria* hybrid disclosed herein has been given the variety denomination 'TSAECH1702'.

CROSS REFERENCE TO RELATED APPLICATIONS

This application claims priority to the Community Plant Variety Rights application number 2017/1147, filed Apr. 25, 2017, which is herein incorporated by reference.

BACKGROUND OF THE INVENTION

Parentage: 'TSAECH1702' is an intergeneric hybrid seedling selection resulting from the controlled pollination of an unnamed *Pachyphytum glutinacaule* plant (not patented), the seed parent, with an unnamed *Echeveria hookeri* plant (not patented), the pollen parent. The crossing was made by the inventor in the autumn of 2013 at a commercial greenhouse in Heerhugowaard, the Netherlands. In the summer of 2015, one seedling was observed which exhibited unique growth and foliage characteristics. The seedling was isolated for further evaluation in order to confirm the distinctness and stability of the characteristics first observed. Upon confirmation of distinctness and stability, 'TSAECH1702' was selected for commercialization in the autumn of 2015.

Asexual Reproduction: Asexual reproduction of the new cultivar 'TSAECH1702', by way of rooting leaf cuttings, was first initiated in the summer of 2016 at the inventor's commercial greenhouse in Heerhugowaard, the Netherlands. Through four subsequent generations, the unique features of this cultivar have proven to be stable and true to type.

SUMMARY OF THE INVENTION

The cultivar 'TSAECH1702' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TSAECH1702'. These characteristics in combination distinguish 'TSAECH1702' as a new and distinct *Pachyveria* cultivar:

1. 'TSAECH1702' exhibits long and narrow succulent foliage with an upright attitude, arranged in basal rosette; and 2. 'TSAECH1702' exhibits thick, spatulate to obovate foliage with an upwardly curved aspect; and
3. 'TSAECH1702' exhibits very light greyed-green juvenile foliage with a white to light blue hue at and near the center of the rosette; and
4. 'TSAECH1702' exhibits foliage which becomes progressively suffused with yellow-green, with age, towards the outer whorls of the rosette; and
5. 'TSAECH1702' exhibits mature foliage at the outermost whorls of the rosette which is generally colored yellow-green with a blue hue.

BOTANICAL DESCRIPTION OF THE PLANT

Figure 1:
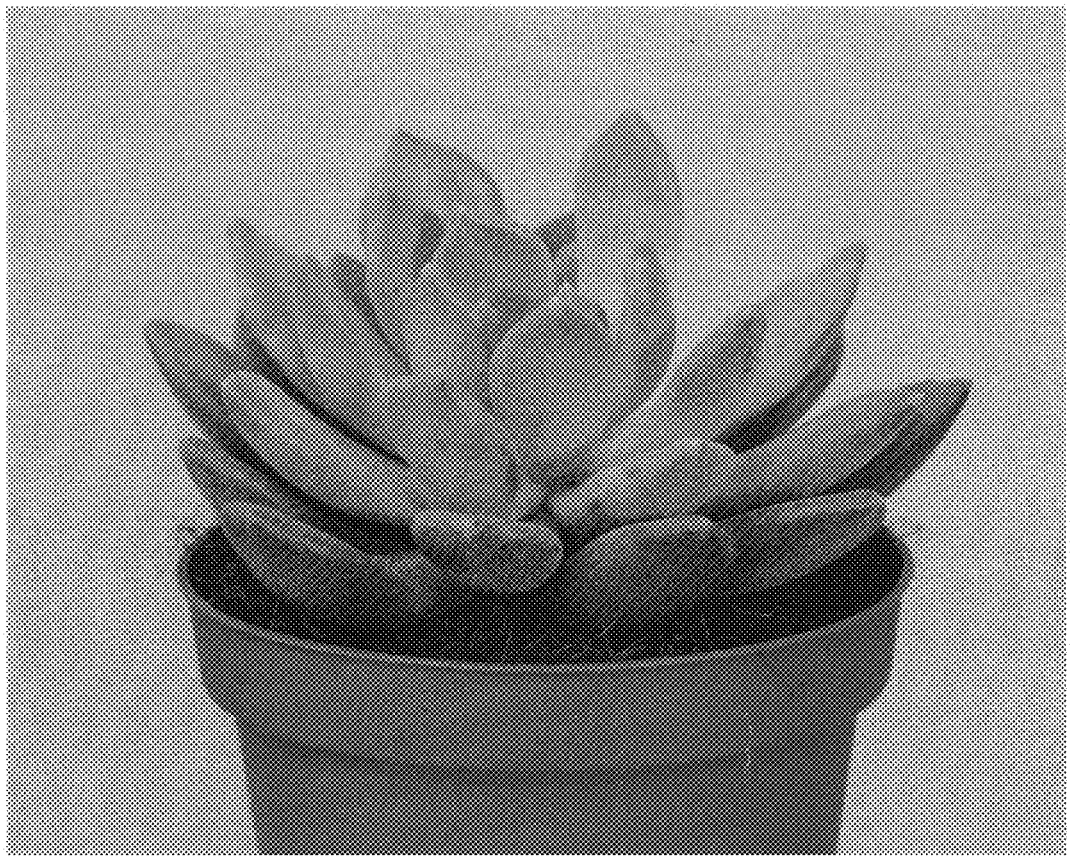
FIG. 1 illustrates, as nearly true as it is reasonably possible to make the same in color photographs of this type, an exemplary plant of 'TSAECH1702' grown in a commercial greenhouse in Heerhugowaard, the Netherlands. This plant is approximately 6 months old, shown planted in a 10 cm container.
Figure 2:
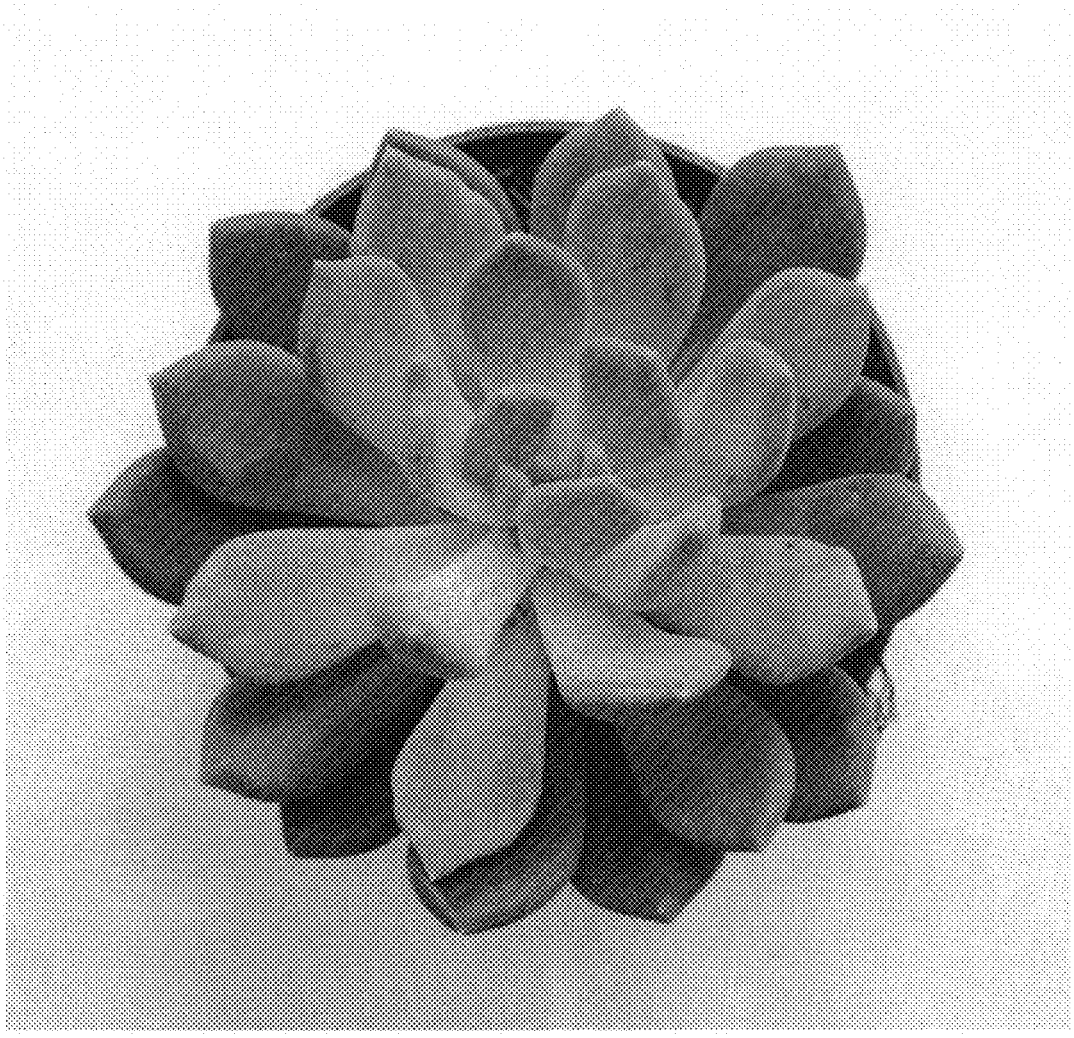
FIG. 2 illustrates, as nearly true as it is reasonably possible to make the same in color photographs of this type, the typical foliage arrangement of 'TSAECH1702.
Figure 3:
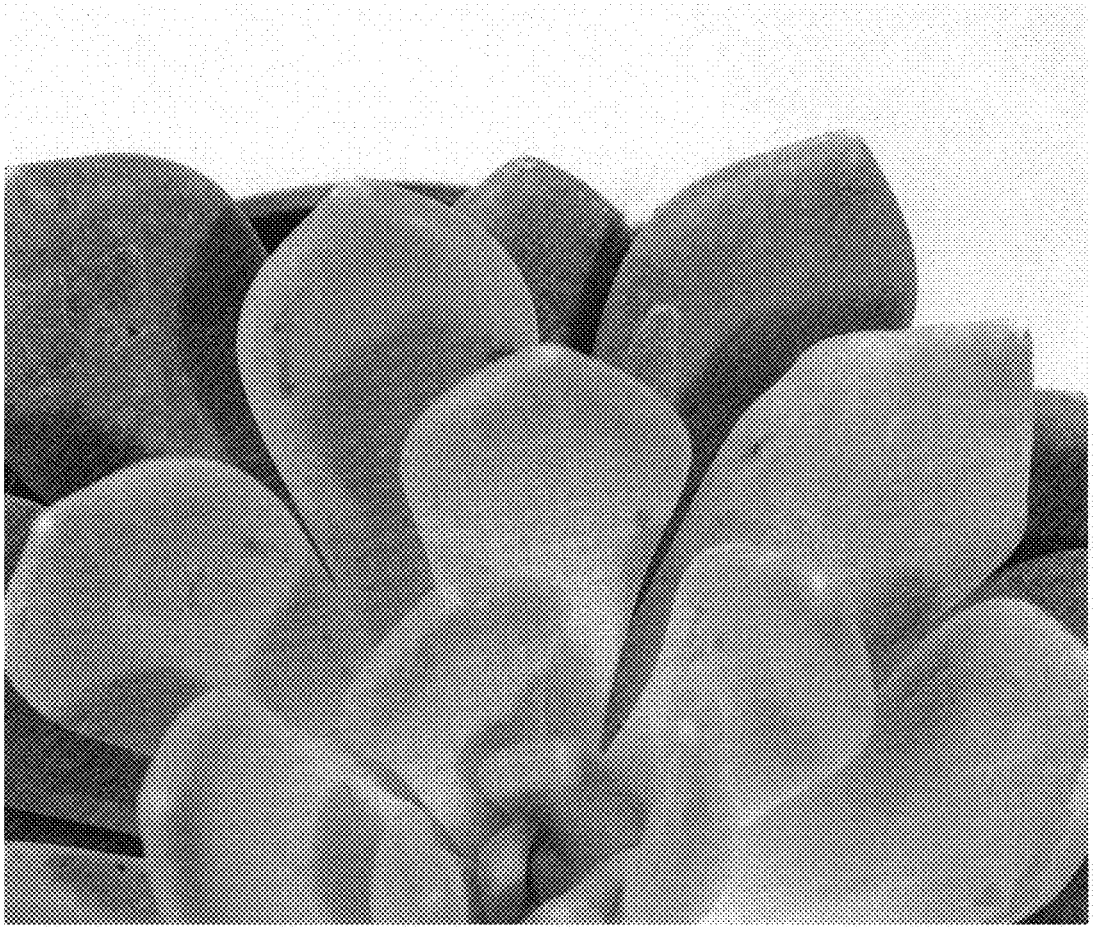
FIG. 3 illustrates, as nearly true as it is reasonably possible to make the same in color photographs of this type, the foliage color from the center of the rosette (juvenile foliage) to the outer most whorl of the rosette (mature foliage) of 'TSAECH1702'.
Figure 4:
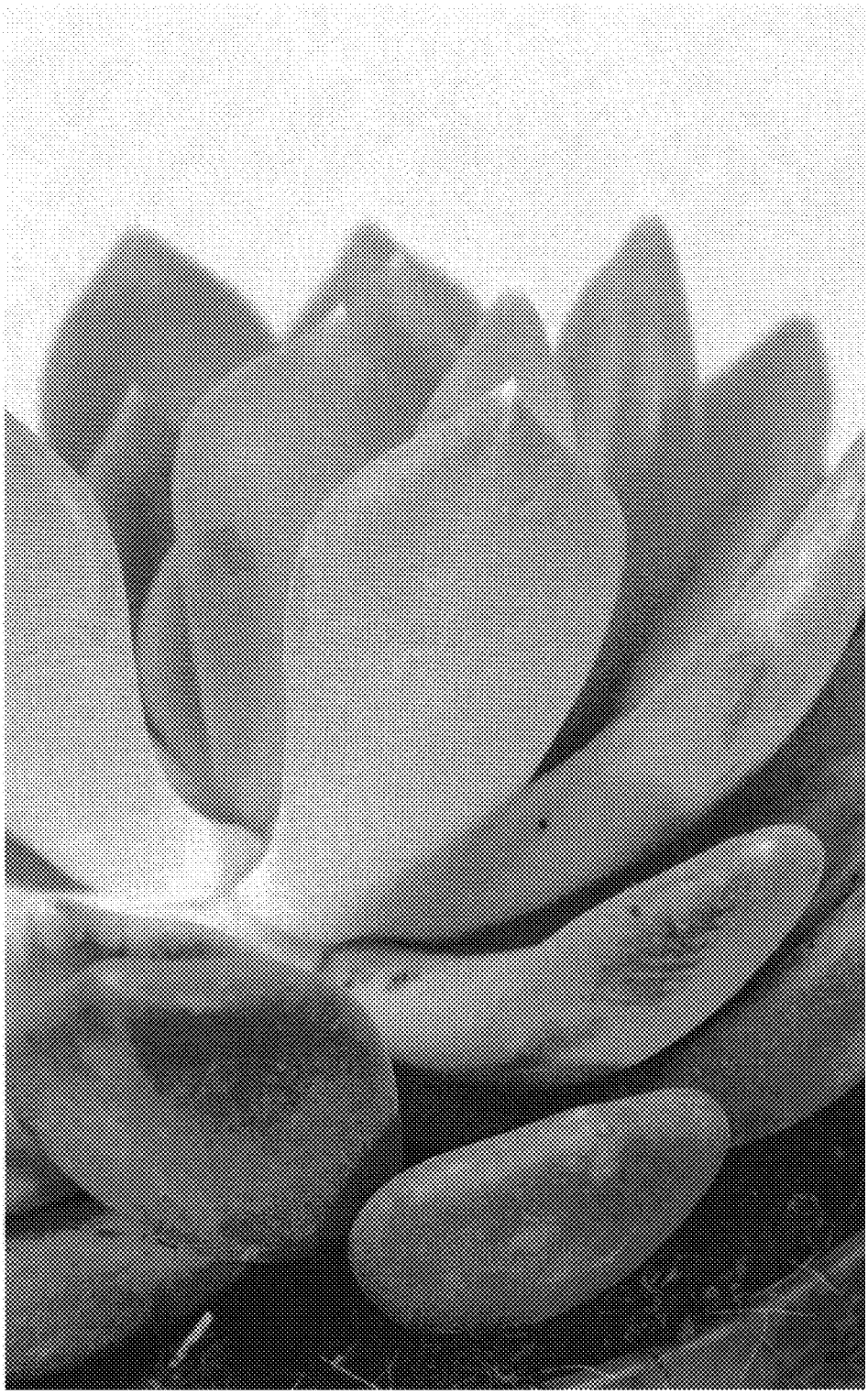
FIG. 4 illustrates, as nearly true as it is reasonably possible to make the same in color photographs of this type, the abaxial surface of the mature foliage 'TSAECH1702'.

The following observations and measurements made in January of 2018 describe averages from a sample set of six specimens of 6 months old 'TSAECH1702' plants grown in 10 cm nursery containers at commercial greenhouse in Heerhugowaard, the Netherlands. Plants were produced using conventional greenhouse production protocols for *Echeveria* and *Pachyphytum* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'TSAECH1702' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'TSAECH1702' and comparisons with the parent plants and closest known comparator are provided below.

Plant description:

*Growth habit.*—Succulent perennial with foliage growing in a non-branched basal rosette.

*Plant shape.*—Flattened globular.

*Height from soil level to top of foliar plane.*—8.4 cm.

*Plant spread.*—Average of 12.0 cm.

*Growth rate.*—Moderate.

*Plant vigor.*—Moderate.

*Propagation.*—Type — Leaf cuttings. Time to initiate rooting — Approximately 21 days at 18 degrees Celsius. Crop time — Approximately 26 weeks to produce a marketable plant in an 11 cm container.

*Disease and pest resistance or susceptibility.*—Neither resistance nor susceptibility to typical *Echeveria* and *Pachyphytum* pests and diseases has been observed.

*Environmental tolerances.*—Adapt to, at least, USDA Zones 10 to 12 and temperatures as high as 40 degrees Celsius; moderate tolerance to rain yet drought tolerant once established; high tolerance to wind.

Root system:

*General.*—Fine, well-branched fibrous roots.

Stems:

*Branching habit.*—Leaves in a non-branching basal rosettes; no main branches or lateral branches present.

Foliage:

*Arrangement.*—Rosette.

*Division.*—Simple.

*Attachment.*—Sessile.

*Quantity.*—Approximately 32 leaves per rosette.

*Shape.*—Thick, succulent leaves which are spatulate to obovate.

*Dimensions.*—6.2 cm long, 2.3 cm wide, and 1.0 cm thick, on average.

*Aspect.*—Very slightly concave and slightly to moderately curved upward.

*Attitude.*—Younger foliage near the center of the rosette is very upright; foliage becoming progressively more relaxed towards the outer whorl of the rosette; average angle of 45 degrees from horizontal.

*Apex.*—Broad acute to apiculate.

*Base.*—Cuneate.

*Margin.*—Entire; not undulated or lobed.

*Pubescence, texture and luster of the adaxial surface.*—Glabrous, smooth, and matte; moderately glaucous.

*Pubescence, texture and luster of the abaxial surface.*—Glabrous, smooth, and matte; moderately glaucous.

*Color.*—Juvenile foliage, adaxial surface — Greyed-green, nearest to RHS 191B, and fading lighter towards the base, nearest to RHS 193C; the epicuticular glaucous wax covering the leaf surface is greyed-green, nearest to RHS 188B. Juvenile foliage, abaxial surface — Greyed-green, nearest to RHS 191B, and fading lighter towards the base, nearest to RHS 193C; the epicuticular glaucous wax covering the leaf surface is greyed-green, nearest to RHS 188B. Mature foliage, adaxial surface — Yellow-green, nearest to RHS 147C, and fading lighter towards the base, nearest to RHS 147D; the epicuticular glaucous wax covering the leaf surface is greyed-green, nearest to RHS 188B. Mature foliage, abaxial surface — Yellow-green, nearest to RHS 147C, and fading lighter towards the base, nearest to RHS 147D; the epicuticular glaucous wax covering the leaf surface is greyed-green, nearest to RHS 188B.

*Venation.*—No venation is visible.

*Petiole.*—No petiole; leaves are sessile.

Inflorescence

No flowering has been observed to date.

Comparisons with the Parent Plant and Closest Known Comparator

Plants of the new cultivar 'TSAECH1702' differ from the seed parent, an unnamed *Pachyphytum glutinicaule* plant (not patented), in the following characteristics described in Table 1 below.

TABLE 1

| Characteristic | 'TSAECH1702' | *Pachyphytum glutinicaule* seed parent. |
|---|---|---|
| General coloration of the foliage. | Light greyed-green with a blue hue. | Light greyed green with a white to pink hue. |
| Leaf thickness. | Thinner. | Thicker. |

Plants of the new cultivar 'TSAECH1702' differ from the pollen parent, an unnamed *Echeveria hookeri* plant (not patented), in the following characteristics described in Table 2 below.

TABLE 2

| Characteristic | 'TSAECH1702' | *Echeveria hookeri* pollen parent. |
|---|---|---|
| General coloration of the foliage. | Light greyed-green with a blue hue. | Light greyed green with a white hue. |
| Leaf thickness. | Thinner. | Thicker. |

Comparisons with the Closest Known Comparator

Plants of the new cultivar 'TSAECH1702' differ from the closest known commercial comparator, *Graptoveria* 'Debbie' (not patented), in the following characteristics described in Table 3 below.

TABLE 3

| Characteristic | 'TSAECH1702' | *Graptoveria* 'Debbie' |
|---|---|---|
| Plant vigor. | More vigorous. | Less vigorous. |
| General coloration of the foliage. | Light greyed-green with a blue hue. | Greyed-green with a pink hue. |

That which is claimed is:

1. A new and distinct variety of *Pachyphytum glutinacaule* x *Echeveria hookeri* hybrid plant named 'TSAECH1702', substantially as described and illustrated herein.

* * * * *